United States Patent
Shah et al.

(10) Patent No.: US 10,987,091 B2
(45) Date of Patent: Apr. 27, 2021

(54) SYSTEM AND METHOD FOR CATHETER CONNECTIONS

(71) Applicant: Biosense Webster (Israel) Ltd., Yokneam (IL)

(72) Inventors: Kruti Shah, Mission Viejo, CA (US); Adrian Contreras, Downey, CA (US); Eduardo Jimenez, Fullerton, CA (US); Itzhak Fang, Irvine, CA (US); Alexander Lifshitz, Arcadia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/157,150

(22) Filed: May 17, 2016

(65) Prior Publication Data

US 2017/0333013 A1    Nov. 23, 2017

(51) Int. Cl.
| | |
|---|---|
| *A61B 17/00* | (2006.01) |
| *A61B 90/30* | (2016.01) |
| *A61B 5/042* | (2006.01) |
| *G08B 5/02* | (2006.01) |
| *G08B 5/36* | (2006.01) |
| *A61B 5/0402* | (2006.01) |
| *H01R 13/717* | (2006.01) |

(Continued)

(52) U.S. Cl.
CPC ............ *A61B 17/00* (2013.01); *A61B 5/042* (2013.01); *A61B 18/1492* (2013.01); *A61B 90/30* (2016.02); *A61B 90/37* (2016.02); *G08B 5/02* (2013.01); *G08B 5/36* (2013.01); *H01R 13/7175* (2013.01); *A61B 5/0402* (2013.01); *A61B 2017/00199* (2013.01); *A61B 2034/252* (2016.02); *A61B 2562/226* (2013.01); *A61B 2562/227* (2013.01); *A61M 2025/0166* (2013.01); *H01R 2201/12* (2013.01)

(58) Field of Classification Search
CPC ...................................................... A61B 17/00
See application file for complete search history.

(56) References Cited

U.S. PATENT DOCUMENTS

| | | |
|---|---|---|
| 5,391,199 A | 2/1995 | Ben-Haim |
| 5,471,982 A | 12/1995 | Edwards |
| (Continued) | | |

FOREIGN PATENT DOCUMENTS

| | | |
|---|---|---|
| WO | 96/05768 | 2/1996 |
| WO | 96/06349 | 2/1996 |
| (Continued) | | |

OTHER PUBLICATIONS

European Search Report and Written Opinion for European Application No. 17171218.5, dated Oct. 9, 2017.

(Continued)

*Primary Examiner* — Joseph H Feild
*Assistant Examiner* — Pameshanand Mahase
(74) *Attorney, Agent, or Firm* — Dergosits & Noah LLP; Todd A. Noah

(57) ABSTRACT

A console for performing a medical procedure has connection ports for electrically coupling equipment. Each connection port may have an associated indicator that signals whether a piece of equipment should be connected to the respective connection port. The indicators may be selectively activated depending on the procedure being performed with the console.

19 Claims, 3 Drawing Sheets

(51) Int. Cl.
  *A61B 90/00* (2016.01)
  *A61B 18/14* (2006.01)
  *A61B 34/00* (2016.01)
  *A61M 25/01* (2006.01)

(56) References Cited

U.S. PATENT DOCUMENTS

| | | | |
|---|---|---|---|
| 5,718,241 | A | 2/1998 | Ben-Haim |
| 6,226,542 | B1 | 5/2001 | Reisfeld |
| 6,301,496 | B1 | 10/2001 | Reisfeld |
| 6,835,082 | B2 | 12/2004 | Gonnering |
| 6,892,091 | B1 | 5/2005 | Ben-Haim |
| 7,536,218 | B2 | 5/2009 | Govari |
| 7,756,576 | B2 | 7/2010 | Levin |
| 7,766,693 | B2 | 8/2010 | Sartor et al. |
| 8,449,318 | B2 | 5/2013 | Beller et al. |
| 8,473,074 | B2 | 6/2013 | North et al. |
| 8,721,539 | B2 | 5/2014 | Shohat et al. |
| 8,731,679 | B2 | 5/2014 | Ternes et al. |
| 8,870,812 | B2 | 10/2014 | Alberti et al. |
| 8,909,320 | B2 | 12/2014 | Jenkins et al. |
| 2003/0125780 | A1* | 7/2003 | Belden ............... A61N 1/056 607/37 |
| 2005/0124980 | A1* | 6/2005 | Sanders ............ A61M 39/0208 604/891.1 |
| 2005/0182466 | A1* | 8/2005 | Mahajan ............... A61N 1/08 607/116 |
| 2007/0016007 | A1 | 1/2007 | Govari et al. |
| 2007/0208338 | A1* | 9/2007 | Eggers ............... A61B 18/1402 606/45 |
| 2008/0248685 | A1* | 10/2008 | Sartor ............... A61B 18/1206 439/489 |
| 2009/0062786 | A1* | 3/2009 | Garito ................ A61B 18/12 606/37 |
| 2009/0099552 | A1 | 4/2009 | Levy et al. |
| 2011/0003516 | A1 | 1/2011 | Daesohner et al. |
| 2011/0045680 | A1* | 2/2011 | Beller ................ A61B 18/14 439/188 |
| 2011/0270065 | A1* | 11/2011 | Ternes ............... A61N 1/36114 600/373 |
| 2012/0278144 | A1* | 11/2012 | Popilock ............... G16H 40/63 705/14.4 |
| 2012/0317287 | A1* | 12/2012 | Amitai ................ H04L 61/103 709/225 |
| 2013/0536962 | | 2/2013 | Barron et al. |
| 2013/0144227 | A1 | 6/2013 | Locke et al. |
| 2014/0125482 | A1* | 5/2014 | Rigsby ............... A61B 17/7001 340/539.13 |
| 2014/0350655 | A1 | 11/2014 | North et al. |
| 2017/0172675 | A1* | 6/2017 | Jarc ..................... A61B 90/361 |

FOREIGN PATENT DOCUMENTS

| | | |
|---|---|---|
| WO | 97/24981 | 7/1997 |
| WO | 01/22536 | 3/2001 |

OTHER PUBLICATIONS

European Examination Report for EP Appln. No. 17171218.5; dated Feb. 6, 2019.

* cited by examiner

SYSTEM AND METHOD FOR CATHETER CONNECTIONS

FIELD OF THE PRESENT DISCLOSURE

This invention relates to electrophysiologic (EP) catheters for mapping and/or ablation in the heart, in particular, to the connections between such catheters and the console used for controlling the delivery of ablation energy, diagnosing detected signals and/or imaging the patient's anatomy.

BACKGROUND

Medical catheterizations are routinely carried for many procedures. In one representative example, cardiac arrhythmias including atrial fibrillation may be diagnosed as well as treated by employing a variety of catheters to access the patient's heart in a minimally invasive manner. Diagnosing such conditions may involve mapping the cardiac tissue to locate aberrant electrical pathways and currents within the heart, as well as to determine mechanical and other aspects of cardiac activity. Various methods and devices have been described for mapping the heart. Such methods and devices are described, for example, in U.S. Pat. Nos. 5,471,982, 5,391,199 and 5,718,241 and in PCT patent publications WO94/06349, WO96/05768 and WO97/24981. These techniques may employ catheters having electrodes for sensing cardiac electrical activity and as well as sensors for determining the position of the catheter relative to an externally-applied magnetic field. By determining the electrical activity at a plurality of locations and determining the spatial coordinates of the locations, a three dimensional (3D) map including the sampled points may be produced. Correspondingly, treatment of arrhythmia may rely on such maps to identify areas for treatment, which may include selectively ablating cardiac tissue by application of energy, e.g., radiofrequency energy via a catheter. The formation of nonconductive lesions may block or modify the propagation of unwanted electrical signals from their origin to help restore more normal function.

To coordinate the procedures described above, as well as others, a console may be provided with processing capabilities to receive and transmit signals associated with mapping or treatment. One or more catheters, each of which may exhibit wide variability in capability and function, may be connected to the console to supply or deliver electrical signals as warranted depending on the procedure being performed. For example, a mapping catheter may employ one or more diagnostic electrodes to sample electrical activity. Notably, many designs employ an electrode array, such as in a basket configuration, to record the signals at multiple locations simultaneously. Likewise, an ablation catheter may be configured to deliver energy to one or more locations, to perform focal ablation or linear ablation, respectively. Both types of catheters may employ position sensors to determine the position and orientation of the electrodes. Still further, depending on the desired functionality, a catheter may have any number of other sensors, such as temperature sensors and/or contact sensors, as well as other components that may require electrical connection to the console. In addition to catheters, a wide variety of other equipment including external positioning sensors, irrigation pumps, ultrasound transducers, electrocardiogram leads and others may also require connection to the console.

Therefore, it will be appreciated that the console must offer a relatively large number of ports or other types of connectors in order to perform its intended role in coordinating and enabling different procedures using different equipment, yet only a subset of the ports may in use during a given procedure. Accordingly, a user must match multiple cables with the appropriate ports and one or more ports may remain unconnected. In light the current trend of increasing numbers and types of catheters or other equipment that may be in potential use, the console connections will likely become yet more complicated.

Prior art attempts to reduce confusion associated with connecting equipment to the console have involved color coding the associated cables and ports. Other conventional attempts employ keyed connectors, so that a given piece of equipment will only couple with the correct port. Although such techniques may reduce the potential of connecting a piece of equipment to the wrong port, the risk of connecting additional equipment that may not be required for a procedure remains. Further, there is no immediate feedback when a necessary piece of equipment has not been connected, and the absence may not be noticed until after the equipment is needed, at which point correction may be more difficult.

What has been needed are systems and methods for reducing confusion associated with connecting catheters and other equipment to a console. It would be desirable to provide indication of which ports should be in use for the procedure being performed. It would also be desirable to provide ready indication when a necessary piece of equipment has not been connected. The techniques of this disclosure as described in the following materials satisfy these and other needs.

SUMMARY

The present disclosure is directed to a console for performing a medical procedure having a plurality of connection ports for electrically coupling a corresponding plurality of pieces of equipment, wherein at least one of the plurality of connection ports is configured to electrically couple a catheter that has at least one electrode. A plurality of indicators are provided, such that each indicator is associated with one of the plurality of connection ports and is configured to signal whether a piece of equipment should be connected to the associated connection port.

In one aspect, at least one of the indicators may be a visual indicator. The visual indicator may be an illuminable light.

In one aspect, at least one of the indicators may be a mechanical indicator. The mechanical indicator may be a sliding shield that covers the associated connection port. Alternatively, the mechanical indicator may be an extending connector of the associated connection port.

In one aspect, the console may have a processor to control the plurality of indicators. The console may also have a memory for storing a database of procedures and equipment required for each procedure, such that the processor may control the plurality of indicators based at least in part on which procedure is being performed. The console may also include a user input for specifying which procedure is being performed.

This disclosure is also directed to a method for connecting equipment to a console for performing a medical procedure. The method may involve providing a console having a plurality of connection ports for electrically coupling a corresponding plurality of pieces of equipment and a plurality of indicators, wherein each indicator is associated with one of the plurality of connection ports, and signaling with each indicator whether a piece of equipment should be connected to the associated connection port.

In one aspect, a catheter having at least one electrode may be electrically coupled to the console in response to the signal.

In one aspect, signaling with at least one of the indicators may involve providing a visual indication. Providing the visual indication may involve illuminating a light.

In one aspect, signaling with at least one of the indicators may involve providing a physical indication. Providing the physical indication may involve selectively exposing the associated connection port with a sliding shield. Alternatively, providing the physical indication may involve selectively extending a connector of the associated connection port from a recessed position.

In one aspect, a subset of the indicators may be selectively activated. The subset of indicators that are selectively activated may be based at least in part on a procedure being performed with the console. For example, the procedure being performed with the console may be specified.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
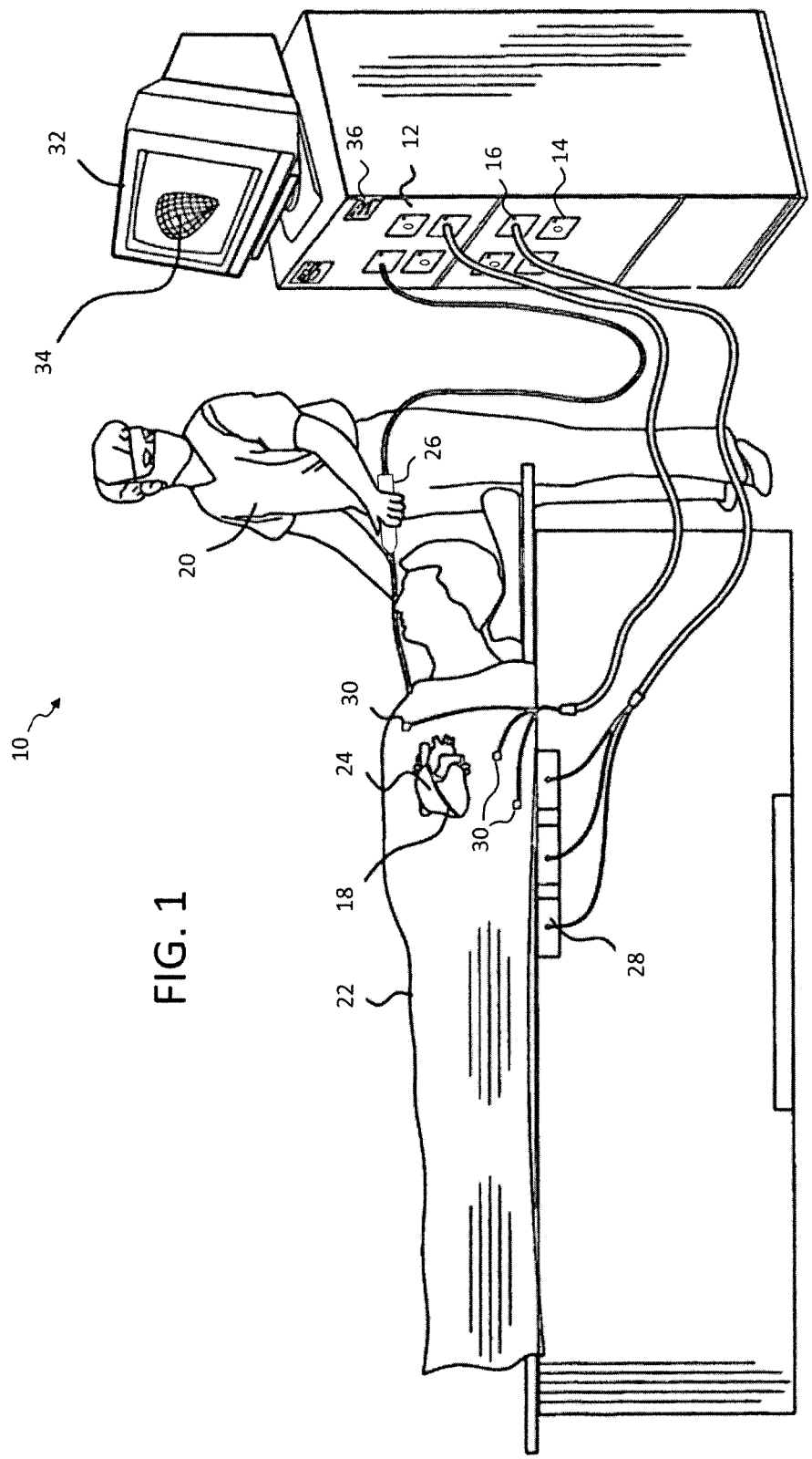
FIG. 1 is a schematic pictorial illustration of a system for performing a medical procedure in the heart, according to one embodiment.
Figure 2:
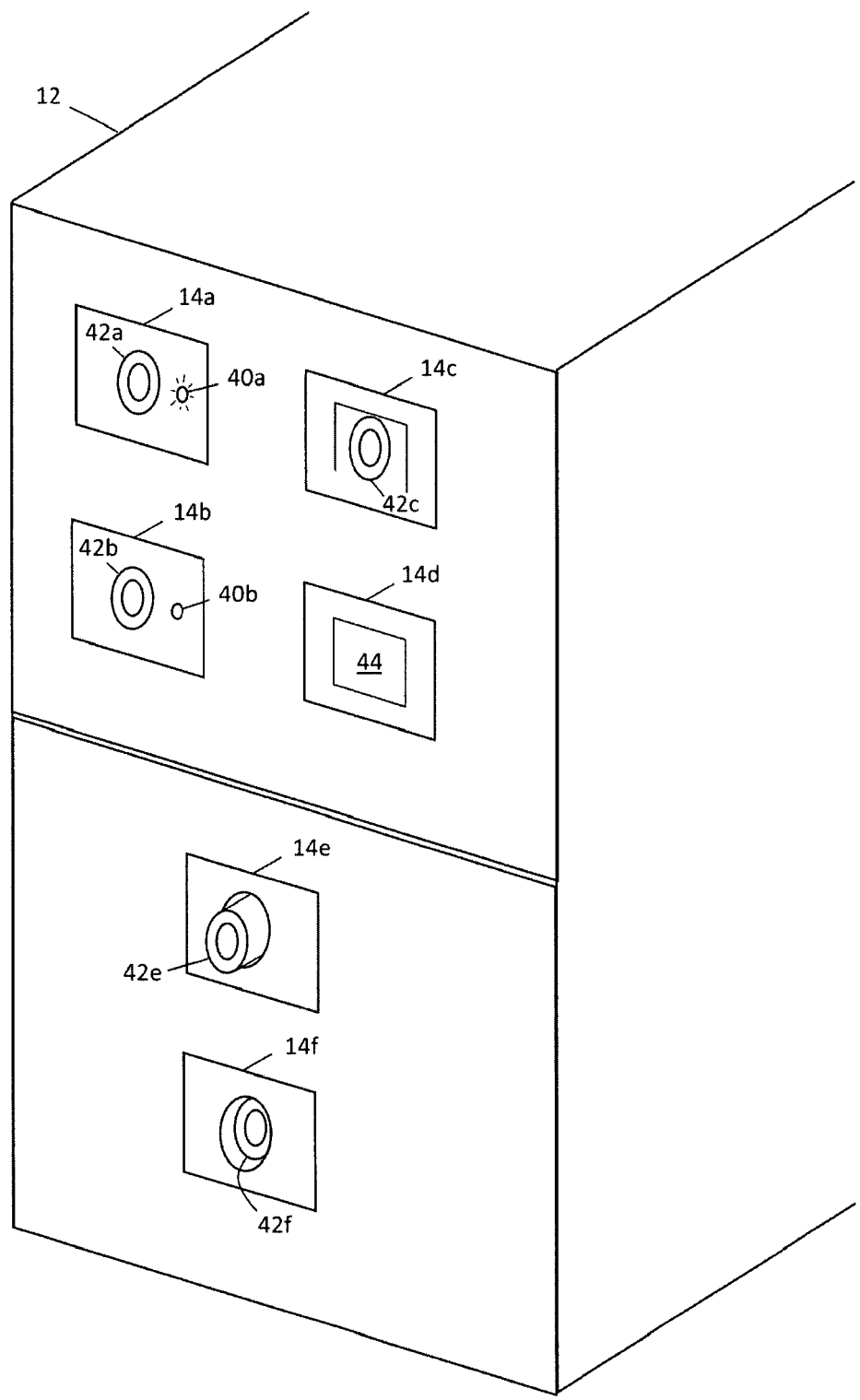
FIG. 2 is a perspective view of a console for performing a medical procedure having connection ports with indicators, according to one embodiment.

To help illustrate aspects of this disclosure, FIG. 2 is a pictorial illustration of a system 10 for performing exemplary catheterization procedures on a heart 12 of a patient. A console 12 has multiple ports 14 to allow for connection with equipment that may be required depending on the procedure being performed. The ports 14 have associated indicators 16 for signaling whether each individual port should be connected to a corresponding piece of equipment. As will be described below, the indicators 16 may be selectively activated to convey whether equipment should be connected to the respective ports according to the procedure being performed.

A processor in the console 12, typically a computer with appropriate signal processing circuits, may receive electrical signals from equipment connected to ports 14 from which electrical activation maps, anatomic positional information, i.e., of the distal portion of the catheter, and other functional images may be prepared, such as according to the methods disclosed in U.S. Pat. Nos. 6,226,542, and 6,301,496, and 6,892,091, whose disclosures are herein incorporated by reference. The processor in console 12 may also control a radiofrequency generator to deliver energy to one or more locations within the patient depending on the procedure, as well as control and/or receive signals from various other equipment that may be used during the procedure. One commercial product embodying elements of the system 10 is available as the CARTO® 3 System, available from Biosense Webster, Inc. (Diamond Bar, Calif.), which is capable of producing electroanatomic maps of the heart as required. This system may be modified by those skilled in the art to embody the principles of the invention described herein.

Without limitation, system 10 may include a catheter 18, which is percutaneously inserted by an operator 20 through the vascular system of a patient 22 into a chamber or vascular structure of the heart 24. The catheter 18 typically comprises a handle 26, having suitable controls on the handle to enable the operator 20 to steer, position and orient the distal end of the catheter as desired. The distal portion of the catheter 18 may contain position sensors (not shown) that provide signals to the processor of console 12 through a connection at one of the ports 14, so that the position, orientation and/or shape of the catheter 18 within the patient 22 may be sensed. The connection may also couple one or more electrodes on the catheter 18, as well as other sensors, such as temperature and/or contact sensors, or other components depending on the application. For example, diagnostic electrodes may be used to measure electrical characteristics of the cardiac tissue and ablation electrodes may deliver energy to form lesions. In some embodiments, one electrode may be employed to perform both functions. As an illustration, areas may be determined to be abnormal, for example by obtaining electrical activation maps using electrodes on the catheter 18, and then may be ablated by application of thermal energy, e.g., by passage of energy radiofrequency electrical current from the radiofrequency generator through wires to one or more electrodes on the catheter 18.

In conjunction with the position sensors of the catheter 18, magnetic field generator coils 28 may be driven by the console 12 through a connection at one of the ports 14. The projected magnetic field induces electrical signals in the coils of the position that may be indicative of their position and orientation in the magnetic fields. These signals are conveyed to the processer of the console 12 for analysis through the connection at one of the ports 14. Alternatively, the position sensors may be driven in order to be sensed by coils 28. The catheter 18 may also be configured to provide position information through techniques such as impedance sensing. The console 12 may be coupled through yet another of the ports 14 to body surface electrodes 30. Tissue impedance may be measured using any suitable technique, such as those taught in U.S. Pat. Nos. 7,536,218 and 7,756,576, which are hereby incorporated by reference.

The console 12 may also include a display 32, which may be used to provide a graphical representation 34 of the relationship of the catheter 18 to the patient's heart. Further, the console 12 may have one or more input devices, such as a keypad 36, that may be used by the operator to specify the procedure being performed and any associated parameters, as well as other relevant information.

The system 10 may also include other equipment that is connected to and controlled by the console 12 via the ports 14, not shown in this embodiment for the sake of simplicity. For example, an ECG monitor may receive signals from one or more body surface electrodes, so as to provide an ECG synchronization signal, as well as other sensors used to measure characteristics of the patient. The system may also include a reference position sensor, on an externally-applied reference patch attached to the exterior of the subject's body or on an internally-placed catheter inserted into heart 24 and maintained in a fixed position relative to the heart, either of which may be connected to the console 12 by one or more of the ports 14. By comparing the position of catheter 18 to that of the reference catheter or patch, its coordinates may be accurately determined relative to the heart, irrespective of heart motion. Other illustrative examples of equipment that may be connected to the console 12 through the ports 14 include, without limitation, an irrigation pump used to supply fluid to manage the heat generated by tissue ablation, an ultrasound imaging transducer, and others.

In light of the wide variety and multiple combinations of equipment that may be connected to the console 12, each port may be associated with an indicator as shown in greater detail in FIG. 2. As desired, each of the indicators may be configured to provide a positive indication of whether a piece of equipment should be connected to the port for the procedure being performed. As a first example, port 14a is equipped with a visual indicator in the form of a light 40a, schematically shown as being illuminated or otherwise activated to convey that a piece of equipment should be coupled to a connector 42a of port 14a. For comparison, the indicator light 40b of port 14b is schematically shown to be off so that it may be understood that no equipment should be connected to port 14b. In other embodiments, any other suitable visual display may be used, either illuminated or not. As a non-limiting example, a liquid crystal display or the like may be used to designate positively or negatively whether equipment should be connected to the port. It should be appreciated that any suitable passive indicator may be used to visually communicate the connection information.

A second example of indicator 16 is a mechanical indicator, such that ports 14c and 14d are equipped with a sliding shield 40, which may be actuated to selectively expose or conceal the port. In the depicted embodiment, the shield has been activated and withdrawn for port 14c and therefore is not visible. Exposure of connector 42c indicates that a connection should be made. In comparison, shield 44 covers the connector (which correspondingly is not visible in this illustration) of port 14d, preventing a user from connecting equipment to the port. As will be appreciated, this embodiment provides a physical indication as well as a visual indication of the connection information, as the user can see whether the shield is deployed in addition to the connection being mechanically obstructed. A third example is another mechanical indicator and is shown in the context of ports 14e and 14f. Notably, connectors 42e and 42f are configured to extend or retract to indicate whether equipment should be coupled. As shown, connector 42e is extended, indicating that equipment should be connected. Conversely, connector 42f is retracted and in a recessed position to indicate that equipment should not be connected. This configuration also provides both physical and visual indication of the connection status of a port. In other embodiments, any suitable mechanical actuation may be employed either to make a connector available, thus indicating that equipment should be connected, or unavailable, indicating that equipment should not be connected.

Figure 3:
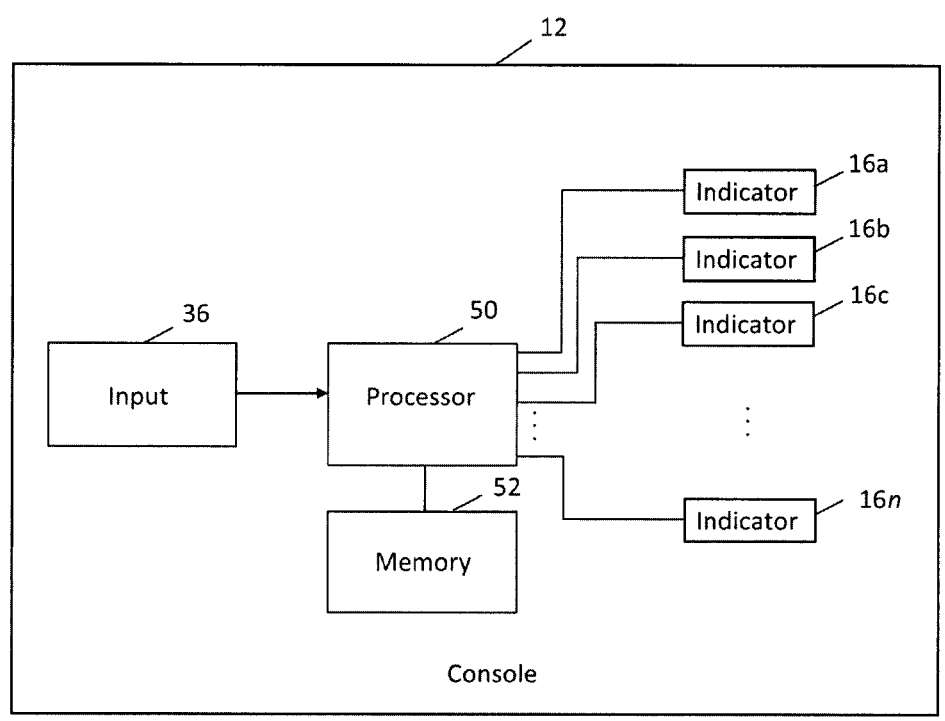
FIG. 3 is a schematic diagram of a console having connection ports with indicators, according to one embodiment.

The schematic representation of console 12 shown in FIG. 3 provides one embodiment for implementing ports with indicators according to the techniques of this disclosure. Relevant components of console 12 are depicted with high level schematic blocks representing their functions. As shown, console 12 include a processor 50 as described above for signal processing as well as controlling the various pieces of equipment that may be coupled to console 12 via the ports 14. Although depicted as a single processor, any number of processors or equivalent computing resources may be employed as desired. Processor 50 may be coupled by an appropriate bus to memory 52, which may store algorithms, routines or other instructions as warranted by the functional requirements of console 12. In the context of this disclosure, memory 52 may store a database of procedures that may be facilitated by console 12, along with the required combination of equipment for each procedure. Processor 50 may also receive information from user input, such as keypad 36 described above, but any suitable user interface may be employed. A manual mode may also be provided to enable the user to specify which equipment will be used for a given procedure.

When employing console 12, the user may input the procedure being performed and any relevant parameters. Based on the information stored in memory 52, processor 50 may control indicators 16a-16n to convey with equipment should be connected to the respective ports 14. Thus, a subset of the indicators may selectively be activated to convey that equipment should be connected to the associated ports, while the remainder of the indicators are not activated and correspondingly convey that equipment should not be connected. A characteristic pattern of which indicators are activated and which are deactivated may be associated with different procedures. As will be appreciated, any number n of indicators may be employed and, in general, an indicator may be provided for each port as desired. As discussed above, control of indicators 16 may be tailored to the type of indicator being used. For lights 40a and 40b, for example, processor 50 may simply control whether they are illuminated. For other types of visual indicators, processor 50 may control the display as necessary to convey whether equipment should be attached to the corresponding port. Likewise, for shield 44 or extendable connectors 42e and 42f, processor 50 may control mechanical actuators to achieve the desired port configuration to indicate whether equipment should be connected. In general, the indicator may be considered activated when it signals that a piece of equipment should be connected to the associated port and may be considered deactivated when it signals that a piece of equipment should not be connected to the associated port.

Accordingly, under the control of processor 50, each port 14 having an indicator 16 may selectively inform the user whether equipment should be connected. As such, confusion associated with connecting catheters and other equipment to console 12 may be reduced by utilizing the techniques of this disclosure. Activation of the indicators provides a positive indication of which ports should be in use for the procedure being performed. Further, since it is readily apparent when an indicator has been activated, the operator may immediately determine when a piece of equipment needed for a procedure has not been connected, given that the associated port will have an activated indicator and nothing coupled to the port.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A console for performing a medical procedure, comprising a plurality of connection ports for electrically coupling a corresponding plurality of pieces of equipment, wherein at least one of the plurality of connection ports is configured to electrically couple a catheter that has at least one electrode, and a plurality of indicators located on the console, wherein each indicator is associated with and adjacent to one of the plurality of connection ports and, in response to input of the medical procedure, each indicator is configured to provide either a positive or negative indication as to whether a piece of equipment should be connected to the associated connection port on the console prior to such connection being made and before performing the medical procedure.

2. The console of claim 1, wherein at least one of the indicators comprises a visual indicator.

3. The console of claim 2, wherein the visual indicator comprises an illuminable light.

4. The console of claim 1, wherein at least one of the indicators comprises a mechanical indicator.

5. The console of claim 4, wherein the mechanical indicator comprises a sliding shield that covers the associated connection port.

6. The console of claim 4, wherein the mechanical indicator comprises an extending connector of the associated connection port.

7. The console of claim 1, further comprising a processor to control the plurality of indicators.

8. The console of claim 7, further comprising a memory storing a database of procedures and equipment required for each procedure, wherein the processor controls the plurality of indicators based at least in part on which procedure is being performed.

9. The console of claim 8, further comprising a user input for specifying which procedure is being performed.

10. A method for connecting equipment to a console for performing a medical procedure, comprising:
providing a console having a plurality of connection ports for electrically coupling a corresponding plurality of pieces of equipment and a plurality of indicators located on the console, wherein each indicator is associated with and adjacent to one of the plurality of connection ports;
providing the console which medical procedure to perform; and
providing with each indicator a positive and negative indication as to whether a piece of equipment should be connected to the associated connection port on the console prior to such connection being made and before performing the medical procedure.

11. The method of claim 10, further comprising electrically coupling a catheter having at least one electrode to the console in response to the signal.

12. The method of claim 10, wherein signaling with at least one of the indicators comprises providing a visual indication.

13. The method of claim 12, wherein providing the visual indication comprises illuminating a light.

14. The method of claim 10, wherein signaling with at least one of the indicators comprises providing a physical indication.

15. The method of claim 14, wherein providing the physical indication comprises selectively exposing the associated connection port with a sliding shield.

16. The method of claim 14, wherein providing the physical indication comprises selectively extending a connector of the associated connection port from a recessed position.

17. The method of claim 10, further comprising selectively activating a subset of the indicators.

18. The method of claim 17, wherein the subset of indicators that are selectively activated is based at least in part on a procedure being performed with the console.

19. The method of claim 18, further comprising specifying the procedure being performed with the console.

* * * * *